United States Patent [19]
Woods

[11] Patent Number: 4,782,820
[45] Date of Patent: Nov. 8, 1988

[54] IRIS RETAINING DEVICE

[76] Inventor: Randall L. Woods, 2460 East Raynell, Springfield, Mo. 65804

[21] Appl. No.: 111,198

[22] Filed: Oct. 22, 1987

[51] Int. Cl.⁴ ............................................. A61B 17/02
[52] U.S. Cl. ...................................... 128/20; 128/341; 623/4; 623/6
[58] Field of Search ........................ 128/20, 341, 343; 623/4-6

[56] References Cited

U.S. PATENT DOCUMENTS

| 4,387,706 | 6/1983 | Glass | 128/20 |
| 4,452,235 | 6/1984 | Reynolds | 623/5 X |

FOREIGN PATENT DOCUMENTS 990220 1/1983 U.S.S.R. .................... 128/20

*Primary Examiner*—Ronald L. Frinks
*Attorney, Agent, or Firm*—Hovey, Williams, Timmons & Collins

[57] ABSTRACT

An improved, iris retaining device (10) adapted for placement within the pupillary opening of a human eye so as to engage the inner margin (32) of the iris (34), so as to enlarge and maintain the pupillary opening during eye surgery. The device (10) preferably comprises an elongated, arcuate, flexible, resilient body (12) including a generally U-shaped in cross section iris-receiving sidewall; the latter presents an inboard central bight portion (18) and a pair of spaced apart wall sections (20, 22) extending outwardly therefrom. The ends (14, 16) of the body (12) are slidably interengaged, and a drawstring (24) is provided for manually contracting the body (12) for initial placement thereof. After such contraction and initial placement, the drawstring (24) and may be released so that the resilient body (12) expands to engage, expand and protect the margin (32) of the iris (34).

5 Claims, 1 Drawing Sheet

U.S. Patent  Nov. 8, 1988  4,782,820
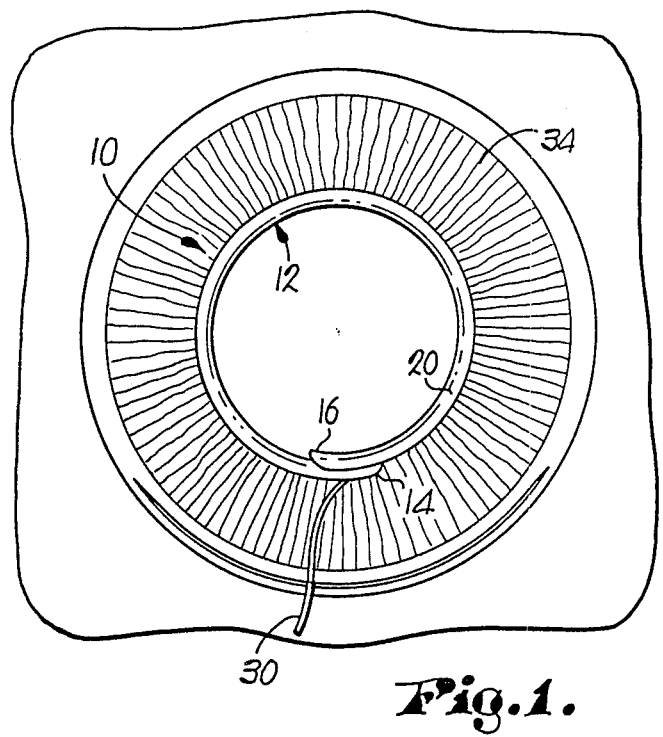
Fig.1.
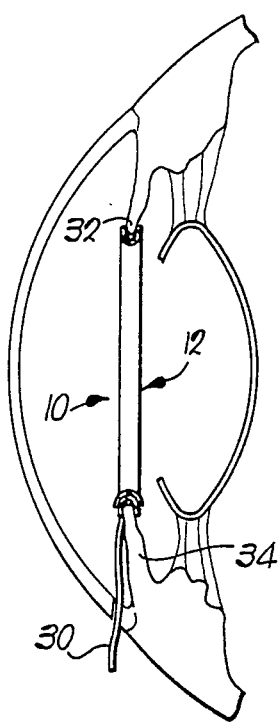
Fig.2.
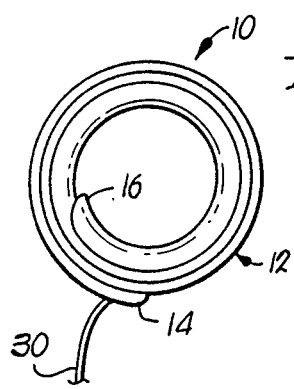
Fig.3.
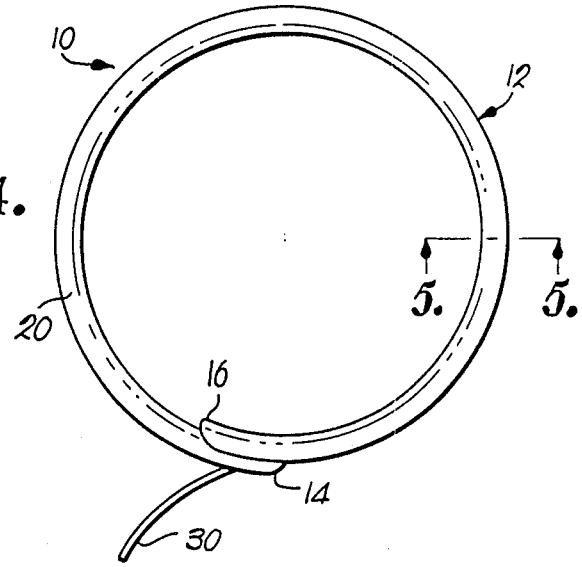
Fig.4.
Fig.5.
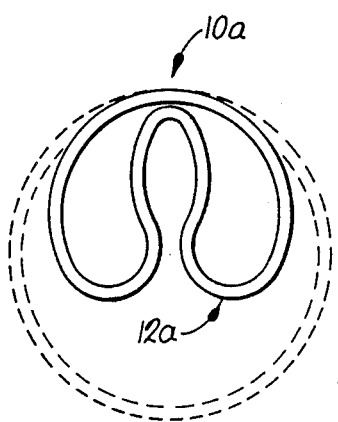
Fig.7.
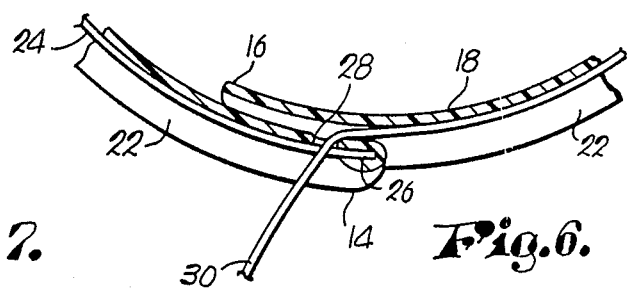
Fig.6.

IRIS RETAINING DEVICE

BACKGROUND OF THE INVENTION

1. Field of the Invention

The present invention is concerned with an iris retaining device adapted for use by eye surgeons in order to enlarge and maintain the pupillary opening of a size to facilitate surgical procedures such as the implantation of intraocular lenses. More particularly, it is concerned with such an iris retaining device which in preferred forms comprises an elongated, arcuate, flexible body size to fit within the inner defining margin of the iris of a human eye and with specially configured sidewall portions for engaging the inner defining margin of the iris.

2. Description of the Prior Art

Modern day treatment for the condition of cataracts very often involves removal of the crystalline lenses of the patient's eye, followed by implantation of replacement lenses. Such intraocular lenses (IOL's) are commonly implanted within the capsule of the eye, behind the iris.

In surgical procedures, the eye surgeon typically dilates the eye, installs instrumentation to maintain the iris in an expanded position, and makes an incision in the anterior wall of the capsule so as to permit removal of the patient's natural lens. At this point, the IOL is inserted and properly emplaced, followed by necessary final sutures in the cornea.

As can be appreciated, surgery of this type involves working in extraordinarily close quarters with a minimum of clearances. One difficult problem confronted by the surgeon in this context is the presence of the iris positioned anteriorly of the capsule and the tendency of the iris to contract and thus create severe clearance problems. The pupillary opening of the human iris is normally 1-3 millimeters in diameter, but during surgery a larger opening is generally necessary, e.g., 7-9 millimeters. As indicated, the conventional technique is to dilate the eye and employ iris-expanding instrumentation, but this is only partially effective.

In addition to clearance problems, the iris may be readily traumatized during eye surgery, resulting from irrigation solutions used to wash out the cortex of the eye, and instrumentation necessary to retract the iris during surgery. Finally, the iris can also be damaged during implantation of an IOL.

SUMMARY OF THE INVENTION

The present invention overcomes the problems outlined above and provides a greatly improved iris retaining device which is small in size and serves to maintain the iris in an expanded condition while at the same time protecting the iris from surgical trauma.

Broadly speaking, the iris retainer of the invention comprises and elongated, arcuate, flexible, resilient body sized to fit within the inner defining margin of the iris of a human eye. The body includes a generally U-shaped in cross section iris-receiving sidewall which presents an inboard central bight portion and a pair of spaced apart wall sections extending outwardly from the bight portion. The U-shaped sidewall is configured for engaging the inner margin of the iris so as to maintain the pupillary opening of an appropriate size to permit surgical procedures. The retainer device may be formed of material such as silicone rubbers, synthetic resins such as polyethylene, or resilient metals such as stainless steel.

In preferred forms, the retainer of the invention is in the form of an elongated body presenting a pair of separable, slidably interengaged ends whereby the body assumes a substantially circular configuration. In this form, means is provided for drawing the ends of the body together so that the device may assume a contracted configuration allowing ready placement thereof within the pupillary opening. Such drawing means is advantageously in the form of a drawstring affixed to one of the ends of the body and extending around the bight portion thereof, with an opening adjacent the one end for passage of the free end of the drawstring therethrough.

In an alternate embodiment, the body presents a continuous circular configuration and is formed of resilient material permitting contraction thereof to facilitate implacement of the device within the pupillary opening.

In use of the retainer devices of the invention, the surgeon first manipulates the body so that the latter assumes a contracted configuration, followed by placement of the contracted body within the pupillary opening; the body is then released, and by virtue of the resilient nature thereof, expands to engage the inner defining margin of the iris and to maintain the same in an expanded condition.

BRIEF DESCRIPTION OF THE DRAWINGS

FIG. 1 is a greatly expanded elevational view depicting an iris retainer in accordance with the invention operatively positioned within a human eye;

FIG. 2 is a fragmentary side view in partial vertical section illustrating the retainer device situated within a human eye;

FIG. 3 is an elevational view depicting the contracted configuration of the retainer device illustrated in FIGS. 1-2;

FIG. 4 is an elevational view of the device shown in FIG. 3, but with the device expanded and of a size for use in a human eye;

FIG. 5 is a sectional view taken along line 5—5 of FIG. 4 which illustrates the U-shaped configuration of the device wall;

FIG. 6 is an enlarged, fragmentary vertical sectinal view illustrating the interconnection between the ends of the retainer device depicted in FIGS. 1-5, and showing the use of the drawstring provided with this embodiment; and FIG. 7 is an elevational view illustrating another retainer device in accordance with the invention with the device being shown in full lines in its contracted position, and in phantom in its expanded position.

DESCRIPTION OF THE PREFEERED EMBODIMENTS

Turning now to the drawing, FIG. 4 illustrates an iris retainer device 10 in the form of an elongated, arcuate, flexible, resilient body 12 having a pair of free, interengaged ends 14, 16 so that the body assumes a substantially circular configuration.

The body further presents a substantially U-shaped in cross section continuous irisengaging sidewall including a central, inboard bight portion 18 together with a pair of spaced apart, outwardly extending wall sections 20, 22 (see FIG. 5). In the form illustrated, the body 12 is an integral member formed of any suitable material such as silicon rubber, soft synthetic resin or an appropriate metal.

The device 10 is further provided with a continuous drawstring 24. Referring specifically to FIG. 6, it will be seen that one end 26 of drawstring 24 is secured to end 14 of the body 12, with the drawstring extending around the entirety of the body in engagement with the outer face of bight portion 18. In addition, it will be observed that a string-clearing opening 28 is provided through bight portion 18 adjacent end 14, with the free end 30 of the drawstring 24 passed through opening 28.

In the use of device 10, after initial preparation of the eye (typically involving incision or removal of the posterior wall of the capsule of the eye), the surgeon first grasps the body adjacent end 14 using forceps, and then pulls free end 30 of drawstring 24 so as to in effect wind the body 12 upon itself. This is continued until the body 12 assumes the configuration shown in FIG. 3, i.e., where it is substantially contracted and of a size for ready location within the pupillary opening. At this point the device is placed within the opening and the drawstring released. This allows the body to return to its expanded configuration depicted in FIG. 4, by virtue of the resilient nature of the material of the body.

As the initially contracted body expands, it encounters the inner margin 32 of the iris 34 (see FIGS. 1 and 2). By virtue of the outwardly extending, U-shaped configuration of the body wall, the margin 32 is engaged and received in a relatively closely conforming manner as best seen in FIG. 1, with the effect that the pupillary opening is expanded to a desired diameter.

During surgical procedures in and around the eye, it will be appreciated that the inner margin 32 of the iris is protected from trauma by the implaced device 10. At the conclusion of the surgery, the surgeon can simply remove the device 10 using forceps, whereupon the iris may return to its original configuration.

In the alternative embodiment illustrated in FIG. 7, a device 10a is provided in the form of a continuous, circular body 12a. As in the case of the first embodiment, the body 12a presents an outwardly extending, U-shaped in cross section, iris-receiving sidewall. In this instance however, by virtue of the integral nature of the device 10a, the drawstring 24 and attendant structure is omitted. In order to permit contraction and initial placement of the device 10a, it is formed of suitable material permitting the surgeon to manually contract the same as shown in full lines in FIG. 7. This procedure would of course be done using forceps, which allow placement of the retracted device 10a within the pupillary opening. At this point the surgeon carefully releases the contracted body 12a, and, using forceps, guides the U-shaped sidewall into conforming engagement with the inner margin of the iris.

In preferred forms of the invention, the retaining device should in its expanded, operative position assume a diameter of from about 6 to 10 millimeters. However, it should also be readily contractable to a diameter of from about 2 to 5 millimeters, so as to facilitate initial placement thereof in the pupillary opening.

I claim:

1. An iris retainer for use during eye surgery and comprising and elongated, arcuate, flexible, resilient body sized to fit within the inner defining margin of the iris of a human eye, said body including a generally U-shaped in cross section iris-receiving sidewall presenting an inboard central bight portion and a pair of spaced apart wall sections respectively extending outwardly from said bight portion, said sidewall being configured for engaging the inner margin of the iris of the human eye in order to maintain the pupillary opening of a size to permit surgical procedures.

2. The retainer of claim 1, said body presenting a pair of separable, slidably interengaged ends whereby the body assumes a substantially circular configuration.

3. The retainer of claim 2, including means for drawing the ends of said body together so that the device assumes a contracted configuration which can be placed within the pupillary opening, said drawing means being releasable for permitting the device to expand and come into operative enagement with the inner defining margin of the iris.

4. the retainer of claim 3, said drawing means conprising a drawstring affixed to one of said ends and extending around said bight portion, there being a drawstring-clearing opening adjacent said one end for passage of the free end of the drawstring therethrough.

5. The retainer of claim 1, said body presenting a continuous circular configuration, the body further being formed of resilient material permitting contraction thereof for implacement of the body in a contracted position within said pupillary opening.

* * * * *